(12) United States Patent
Jun et al.

(10) Patent No.: US 7,417,004 B2
(45) Date of Patent: Aug. 26, 2008

(54) CATALYST FOR DIMETHYL ETHER SYNTHESIS AND ITS PREPARATION METHODS

(75) Inventors: Ki-Won Jun, Daejeon (KR); Hyun-Seog Roh, Daejeon (KR); Jae-Woo Kim, Chungcheongnam-do (KR); Jeon Keun Oh, Daejeon (KR); Jin Hwan Bang, Daejeon (KR)

(73) Assignee: SK Energy Co., Ltd., Seoul (KR)

( * ) Notice: Subject to any disclaimer, the term of this patent is extended or adjusted under 35 U.S.C. 154(b) by 223 days.

(21) Appl. No.: 10/572,707

(22) PCT Filed: Aug. 30, 2004

(86) PCT No.: PCT/KR2004/002174

§ 371 (c)(1),
(2), (4) Date: Mar. 17, 2006

(87) PCT Pub. No.: WO2005/028104

PCT Pub. Date: Mar. 31, 2005

(65) Prior Publication Data

US 2007/0117709 A1    May 24, 2007

(30) Foreign Application Priority Data

Sep. 20, 2003    (KR) .................... 10-2003-0065380

(51) Int. Cl.
*B01J 29/06*    (2006.01)
(52) U.S. Cl. .................................. 502/64; 502/71
(58) Field of Classification Search ............ 502/64, 502/71
See application file for complete search history.

(56) References Cited

U.S. PATENT DOCUMENTS

| | | | |
|---|---|---|---|
| 4,536,485 A | 8/1985 | Topp-Jorgensen | 502/62 |
| 4,590,176 A | 5/1986 | Hoek et al. | 502/307 |
| 5,254,596 A | 10/1993 | Irick, Jr. et al. | 518/728 |
| 6,740,783 B1 * | 5/2004 | Jun et al. | 568/698 |

FOREIGN PATENT DOCUMENTS

| | | |
|---|---|---|
| EP | 0 291 937 | 3/1989 |
| JP | 57-007432 | 1/1982 |
| JP | 59-016845 | 1/1984 |
| JP | 59-42333 | 3/1984 |
| JP | 61-017528 | 1/1986 |
| KR | 100228748 | 8/1999 |
| KR | 2000-0002477 | 1/2000 |
| KR | 1020040051032 | 6/2004 |

OTHER PUBLICATIONS

Elnicke et al., "Liquid-phase Adsorption of Ethanol-Water Mixtures on NaZSM-5 Zeolite with Inorganic and Organic Binders", pp. 1283-1286, J. Chem. Soc. Faraday Trans., 1991, 87(8).*

* cited by examiner

*Primary Examiner*—Elizabeth D Wood
(74) *Attorney, Agent, or Firm*—Frommer Lawrence & Haug LLP; Ronald R. Santucci

(57) ABSTRACT

This invention relates to a catalyst for synthesis of dimethyl ether and its preparation methods. More specifically, this invention relates to a catalyst with improved formulation for a highly efficient synthesis of dimethyl ether via dehydration of methanol. These catalysts are composed of hydrophobic zeolites, cations selected from alkali metal, alkaline earth metal, or ammonium along with alumina, silica, or silica-alumina. The methods of manufacturing the catalyst of this invention include (a) combining hydrophobic zeolites and precursors of alkali or alkaline earth metal cations with pastes of inorganic binders (at least one selected from the group consisting of bohemites, silica sol, and clay) and calcining the mixture at high temperature; (b) combining particles, which are obtained by calcining the hydrophobic zeolites impregnated with precursors of alkali or alkaline earth metal cations, with pastes of inorganic binders (at least one selected from bohemites, silica sol, and clay) and calcining the mixture at high temperature; (c) combining hydrophobic zeolites with pastes of inorganic binders (at least one selected from the group consisting of bohemites, silica sol, and clay), calcining the mixture at high temperature, impregnating the calcined product with precursors of ammonium cations and calcining the mixture at high temperature. The catalysts of this invention provide significantly high yields of dimethyl ether because they do not result in the production of hydrocarbon side products and their high catalytic activities are maintained for a prolonged period of time.

17 Claims, No Drawings

CATALYST FOR DIMETHYL ETHER SYNTHESIS AND ITS PREPARATION METHODS

This application is a 371 of PCT/KR2004/002174 filed on Aug. 30, 2004, published on Mar. 31, 2005 under publication number WO 2005/028104 A1 which claims priority benefits from South Korean Patent Application Number 10-2003-0065380 filed Sep. 20, 2003.

TECHNICAL FIELD

This invention relates to a catalyst for the synthesis of dimethyl ether and its preparation methods. More specifically, this invention relates to a catalyst with improved formulation for highly efficient synthesis of dimethyl ether via dehydration of methanol composed of hydrophobic zeolites, cations selected from alkali metal, alkaline earth metal, or ammonium along with alumina, silica, or silica-alumina, and methods of manufacturing the catalyst, which include (a) combining hydrophobic zeolites and precursors of alkali or alkaline earth metal cations with pastes of inorganic binders (at least one selected from the group consisting of bohemites, silica sol, and clay) and calcining the mixture at high temperature; (b) combining particles, which are obtained by calcining the hydrophobic zeolites impregnated with precursors of alkali or alkaline earth metal cations, with pastes of inorganic binders (at least one selected from bohemites, silica sol, and clay) and calcining the mixture at high temperature; (c) combining hydrophobic zeolites with pastes of inorganic binders (at least one selected from the group consisting of bohemites, silica sol, and clay), calcining the mixture at high temperature, impregnating the calcined product with precursors of ammonium cations and calcining the mixture at high temperature.

BACKGROUND ART

Dimethyl ether, one of essential basic chemicals in the chemical industry, has high potentials as an aerosol propellant and as a clean fuel. Currently, the potential of dimethyl ether as a clean alternative fuel for internal combustion has been much increased and thus it is in urgent need to develop a more economical process for its manufacture.

There are two general methods of manufacturing dimethyl ether as follows.

The first method relates to a direct synthesis of dimethyl ether from hydrogen and carbon oxides as delineated in the following equation.

[Equation 1]

$CO_2 + 3H_2 \rightarrow CH_3OH + H_2O$ (1)

$CO + 2H_2 \rightarrow CH_3OH$ (2)

$2CH_3OH \rightarrow CH_3OCH_3 + H_2O$ (3)

$CO + H_2O \rightarrow CO_2 + H_2$ (4)

The manufacturing method of dimethyl ether directly from a gaseous mixture of $H_2/CO/CO_2$ using methanol catalysts and dehydration catalysts in fixed bed reactors are described in East German Pat. No. 291,937, U.S. Pat. No. 5,254,596, etc. Catalysts for methanol synthesis that can be used in the above Equation 1 include $ZnO/Al_2O_3$ and $CuO/ZnO/Al_2O_3$, and zeolites can be used as a dehydrating catalyst (U.S. Pat. No. 4,536,485, Korean Pat. No. 228,748).

The second method involves dehydration of methanol as delineated in the Equation 2.

[Equation 2]

$2CH_3OH \rightarrow CH_3OCH_3 + H_2O$

The synthesis of dimethyl ether via dehydration of methanol as described in the Equation 2 is achieved at 250-450° C. using a solid catalyst. Gamma-alumina (Japanese Laid-Open Pat. Appl. No. 1984-16845) and silica-alumina (Japanese Laid-Open Pat. Appl. No. 1984-42333) are ordinarily used as solid catalysts in a synthesis of dimethyl ether.

The conversion of methanol into dimethyl ether is carried out using an acid catalyst. The activity and selectivity of a catalyst vary depending on the acidity of an acid catalyst because the conversion of methanol into dimethyl ether is an intermediate step in hydrocarbon synthesis.

For instance, in the presence of a catalyst bearing mainly strong acid sites, methanol, after it is converted into dimethyl ether, is proceeded further to generate hydrocarbons as side products. On the other hand, in the presence of a catalyst bearing mainly weak acid sites, the activity of the catalyst becomes low and thus results in insufficient conversion of methanol into dimethyl ether.

The use of a hydrophobic zeolite such as USY, Mordenite, ZSM family, Beta, and others in dehydration reaction of methanol shows a stronger catalytic activity than the use of gamma-alumina at low temperature. However, the strong acidity of such zeolites produce hydrocarbons and cokes as side products during the conversion of methanol into dimethyl ether thereby reducing selectivity. According to the results of the present inventors, conventional H-USY, H-ZSM-5, and H-Beta zeolites are too acidic they produce hydrocarbons as by-products such as methane, ethane, and propane. Further, the hydrocarbon by-products are low molecular weight alkanes with little value and also lead to the deactivation of catalysts via coking.

A method for synthesizing dimethyl ether using crude methanol containing 5-50 mole % water in order to inhibit hydrocarbon production by hydrophobic zeolites has been disclosed by the present inventors (Korean Pat. Appl. No. 2004-51032; U.S. Pat. No. 6,740,783).

DISCLOSURE

The inventors of this invention have kept working on the development of catalysts for dimethyl ether synthesis via dehydration of methanol having high catalytic activity at lower temperatures and not producing hydrocarbons as by-products.

As a result, they found that prolonged catalytic activity can be achieved without deactivation of the catalyst if methanol dehydration is performed in the presence of a catalyst comprising: hydrophobic zeolite; cations selected from the group consisting of alkali metal, alkaline earth metal, and ammonium; and any one selected from alumina, silica, and silica-alumina due to a relatively high catalytic activity without generating hydrocarbon by-products. Further, the inventors found that use of the above catalyst can eliminate too strong acid sites of the catalyst due to the cations s elected from alkali metal, alkaline earth metal, and ammonium. Furthermore, alumina, silica, or silica-alumina can serve as a binder for catalyst-forming as well as a diluent to prevent local increase in temperature within a catalyst particle due to host-pot resulted from exothermic reaction processes thus preventing the generation of hydrocarbon by-products while showing an improved yield of dimethyl ether from methanol.

Therefore, this invention relates to a catalyst that provides high yield of dimethyl ether via dehydration reaction of methanol and the manufacturing methods of the catalyst.

This invention relates to a catalyst used in high yield synthetic process of dimethyl ether via dehydration of methanol comprising (a) hydrophobic zeolite; (b) cations selected from the group consisting of alkali metal, alkaline earth metal, and ammonium; and (c) alumina, silica, or silica-alumina In addition, this invention also comprises the manufacturing processes of the catalyst for the synthesis of dimethyl ether via dehydration of methanol.

Following is a more detailed explanation of this invention.

The catalyst in this invention is a hydrophobic zeolite with its $H^+$ cations partially and adequately replaced with cations selected from the group consisting of alkali metal, alkaline earth metal, and ammonium that eliminate its strong acid sites. This allows a significant improvement in selectivity for dimethyl ether due to maximal inhibition of side reactions that result in the formation of hydrocarbons and cokes.

Further, the formation of hot spots within catalytic particles due to local temperature increases during a dehydration process of methanol is blocked because the alumina, silica, or silica alumina used in this invention acts as diluents. This allows a maximal inhibition of hydrocarbon side products by preventing local temperature increases thus significantly improving the selectivity for dimethyl ether.

Thus, catalysts of this invention allow a highly efficient production of dimethyl ether because they maintain high catalytic activities for prolonged periods without deactivation during a dehydration reaction of methanol.

The catalysts in this invention are composed of (a) hydrophobic zeolite USY, Mordenite, ZSM family, Beta; (b) specific cations that eliminate aforementioned strong acid sites of zeolites; and (c) alumina, silica, or silica-alumina that acts as a diluent for inhibiting local temperature increases within catalyst as well as a binder for catalyst-forming.

The $Na^+$ exchanged Na-type zeolites (Na-ZSM-5, Na-Beta, Na-Mordenite, etc.) and $H^+$ exchanged H-type zeolites (H-ZSM-5, H-Beta, H-Mordenite, etc.) are generally used. However, according to studies by the present inventors, the Na-type zeolites are not efficient in the present reaction because of their weak acidic properties. And, H-type zeolites produce hydrocarbon side products due to their strong acidic properties.

Therefore, the acidities of hydrophobic zeolites of this invention were properly adjusted to maintain maximal acidity for the production of dimethyl ether by adding selective cations within 20-90 mole % range with respect to the $H^+$ ions. That is, the strong acidic properties of H-type zeolites are adjusted by adding sufficient amounts of Na, Mg, or ammonium to convert them into NaH, MgH, and $NH_4$ H-type zeolites.

This invention uses at least one inorganic binder selected from the group consisting of boehmite, silica sol, and clay to dilute the hydrophobic zeolites within a catalyst resulting in inhibition of production of hydrocarbons or cokes caused by hot spots formed by the exothermic reaction on strongly acidic hydrophobic zeolites. The boehmite, silica sol, and clay are converted respectively into alumina, silica, and silica-alumina. Especially, boehmite, silica sol, and clay have the advantage of functioning as binders allowing an easy forming of a catalyst, which is needed when using a catalyst in a fixed bed reactor. An inorganic binder selected from the group consisting of alumina, silica, and silica-alumina for the aforementioned objective of this invention should be in the range of 1:0.1-50 wt ratio based on the zeolite impregnated with cations.

As a result, an application of a catalyst of this invention to the dehydration reaction of methanol allowed to obtain much higher yield of dimethyl ether than the ordinary processes, in spite of not giving formation of hydrocarbon by-product or the deactivation of the catalyst.

Following is the manufacturing process of the aforementioned catalysts for dimethyl ether production.

The hydrophobic zeolites used in the production of the catalyst of this invention include but are not limited to ordinary ones used in this field such as USY, Mordenite, ZSM type, Beta, etc., where the $SiO_2/Al_2O_3$ ratio is in the range of 20-200. A precursor material containing cations selected from the group consisting of alkali metal, alkaline earth metal, and ammonium used to adjust the strong acidity of a hydrophobic zeolite is added as a salt such as a nitrate or a carbonate or as a hydroxide to the zeolite using a conventional impregnation method. Further, the catalyst of this invention can be formed into granules, extrudates, tablets, balls, or pellets, with the forming being done according to conventional methods.

The manufacturing process for the catalysts of this invention can be divided into following three manufacturing methods according to the type of cation used to adjust the strong acidity of a zeolite sample.

The first method of manufacturing the catalyst for dimethyl ether production according to this invention comprises:

(1-i) adding an acidic aqueous solution or water to at least one type of inorganic binder selected from the group consisting of boehmite, silica sol, and clay to obtain a paste;

(1-ii) extrusion of the aforementioned paste to form a shape after adding hydrophobic zeolite particles and alkali or alkaline earth metal salts or hydroxides to it; and (1-iii) drying the formed material, and calcining it at 500-800° C.

The second method of manufacturing the catalyst for dimethyl ether production according to this invention comprises:

(2-i) impregnating an alkali or alkaline earth metal salt or a hydroxide into a hydrophobic zeolite and drying it, followed by calcining it at 400-800° C. to obtain solid particles;

(2-ii) adding an acidic aqueous solution or water to at least one type of inorganic binder selected from the group consisting of boehmite, silica sol, and clay to obtain a paste;

(2-iii) extrusion of the above-mentioned solid particles mixed with the paste to form a shape; and (2-iv) drying the formed material and calcining it at 500-800° C.

The third method of manufacturing the catalyst for dimethyl ether production according to this invention comprises:

(3-i) adding an acidic aqueous solution or water to at least one type of inorganic binder selected from the group consisting of boehmite, silica sol, and clay to obtain a paste;

(3-ii) extrusion of this paste after adding hydrophobic zeolite particles to form a shape; and (3-iii) drying this formed material and calcining it at 500-800° C.;

(3-iv) impregnating an aqueous ammonium hydroxide or ammonium salt solution into the formed material mentioned above; and (3-v) calcining the above impregnated material at 300-400° C.

The first and second manufacturing processes stated above relate to manufacturing of a catalyst by impregnating cations of alkali or alkaline earth metals into zeolite, and the third manufacturing process relates to manufacturing of a catalyst by impregnating ammonium cations into a zeolite.

In the catalyst manufacturing processes stated above, an aqueous acid solution or water is added to at least one of inorganic binders selected from the group consisting of boehmite, silica sol, and clay to obtain a paste. The aqueous acid solution used can be nitric acid, acetic acid, or phosphoric acid. Although sufficient catalyst binding effect can be obtained by using at least one inorganic binder selected from the group consisting of boehmite, silica sol, and clay for the manufacturing of a catalyst of this invention, polyvinyl alcohol, carboxymethyl cellulose, and other traditional organic binders can be used as a supplementary binder or a pore promoter, upon necessity.

These organic binders as supplemental binders can be used in the range of 0-30 wt % of at least one used binder selected from the group consisting of boehmite, silica sol, and clay. These supplemental binders can be added to inorganic binders during the paste manufacturing process, and they can be also added to an inorganic binder paste and zeolite and/or cations such as an alkali metal precursor mixture.

Further, the calcining performed during the catalyst manufacturing process of this invention is a necessary step to establish sufficient infiltration into the zeolite structure of the cation precursors, and the catalysts sought for in this invention can only be obtained when the aforementioned temperature range is maintained.

On the other hand, the following is the general manufacturing method for dimethyl ether via dehydration of methanol on a catalyst obtained via a manufacturing process described above.

After packing a reactor with the catalyst, the catalyst is pretreated before methanol dehydration by passing an inert gas such as nitrogen at a rate of 20-100 mL/g catalyst/min at 100-350° C. Methanol is added to the reactor with the pretreated catalyst. The reaction temperature is maintained at 150-350° C. If the reaction temperature is below 150° C., the reaction speed becomes insufficient thus resulting in low conversion. If the reaction temperature is above 350° C., the formation of dimethyl ether becomes thermodynamically unfavorable thus resulting in low conversion.

The reaction pressure is maintained at 1-100 atmosphere, and a pressure over 100 atmosphere is inappropriate because it causes a problem in the reaction. And, it is preferable that the liquid hourly space velocity (LHSV) for a methanol dehydration reaction be within 0.05-100 $h^{-1}$ based on methanol.

The productivity becomes too low if the LHSV is below 0.05 $h^{-1}$, and the conversion rate becomes too low when the LHSV is above 100 $h^-$ because the contact time with the catalyst decreases.

A fixed bed reactor for the gaseous phase, a fluidized bed reactor, or a liquid phase slurry reactor can be used as a reactor with an equal effect.

As mentioned above, hydrophobic zeolite with adjusted acidity is used as a catalyst in this invention without deactivation of the catalyst during the dehydration of methanol, without production of hydrocarbon by-products, and with a high production yield of dimethyl ether.

Best Mode

This invention is explained in more detail based on the following Examples, but they should not be construed as limiting the scope of this invention.

EXAMPLE 1

H-ZSM-5 ($SiO_2/Al_2O_3$=40) zeolite was impregnated with aqueous sodium nitrate containing $Na^+$ equivalent to 40 mole % of $H^+$ in the zeolite, dried for 12 hours at 120° C., then calcined for 6 hours at 600° C. to obtain a Na—H-ZSM-5. A paste was prepared by adding 2.5% nitric acid (nitric acid solution/zeolite wt. ratio=0.8) to boehmite (boehmite/zeolite wt. ratio=1). To this paste, the above NaH type zeolite particles and water (water/zeolite wt. ratio=0.5) were added and extruded. It was dried at 120° C. for 12 hours and calcined at 600° C. for 6 hours to obtain a catalyst. The boehmite ingredient in the catalyst is converted into gamma-lumina during the calcination at 600° C. for 6 hours.

2.5 mL of this catalyst was transferred to a fixed bed reactor. Nitrogen gas was passed over this at a rate of 50 mL/min, and the reactor temperature was maintained at 270° C. Methanol was passed through the catalytic bed at a LHSV of 25 $h^{-1}$, and the reactor was maintained under 10 atm and at 270° C. The results are shown in Table 1.

EXAMPLE 2

To H-ZSM-5 ($SiO_2/Al_2O_3$=40) zeolite, aqueous sodium nitrate containing $Na^+$ equivalent to 50 mole % of $H^+$ in the zeolite was added. This mixture was combined with a paste prepared by mixing of 2.5% aqueous nitric acid (nitric acid solution/zeolite wt. ratio=0.8) and boehmite (boehmite/zeolite wt. ratio=1). To this mixture paste, water (water/zeolite wt. ratio=0.5) was added and mixed well. It was extruded, dried at 120° C. for 12 hours and calcined at 600° C. for 6 hours to obtain a catalyst.

Then, a dehydration reaction of methanol was performed under the same reaction condition as in Example 1. The results are shown in Table 1.

EXAMPLE 3

H-Beta ($SiO_2/Al_2O_3$=25) zeolite was impregnated with aqueous potassium nitrate containing $K^+$ equivalent to 60 mole % of $H^+$ in the zeolite, dried for 12 hours at 120° C., then calcined for 6 hours at 500° C. to obtain a K—H-Beta. A paste was prepared by adding 2.5% nitric acid (nitric acid solution/zeolite wt. ratio=0.8) to boehmite (boehmite/zeolite wt. ratio=1). To this paste, the above KH type zeolite particles and water (water/zeolite wt. ratio=0.5) were added and extruded. It was dried at 120° C. for 12 hours and calcined at 550° C. for 6 hours to obtain a catalyst.

Then, a dehydration reaction of methanol was performed under same reaction condition as in Example 1. The results are shown in Table 1.

EXAMPLE 4

To H-Mordenite ($SiO_2/Al_2O_3$=35) zeolite, aqueous calcium nitrate containing $Ca^{2+}$ equivalent to 40 eq. % of $H^+$ in the zeolite ($Ca^{2+}/H^+$ mole ratio=0.2) was added. This mixture was combined with a paste prepared by mixing 2.5% aqueous nitric acid (nitric acid solution/zeolite wt. ratio=0.8) and boehmite (boehmite/zeolite wt. ratio=1). To this mixture paste, water (water/zeolite wt. ratio=0.5) was added and mixed well. It was extruded, dried at 120° C. for 12 hours, and calcined at 550° C. for 6 hours to obtain a catalyst.

Then, a dehydration reaction of methanol was performed under same reaction condition as in Example 1. The results are shown in Table 1.

EXAMPLE 5

H-ZSM-5 ($SiO_2/Al_2O_3$=40) zeolite was impregnated with aqueous sodium nitrate and magnesium nitrate containing $Na^+$ and $Mg^{2+}$ equivalent to 20 mole % and 30 eq. % of $H^+$, respectively, in the zeolite ($Mg^{2+}/H^+$ mole ratio=0.15), dried for 12 hours at 120° C., then calcined for 12 hours at 550° C. to obtain a Na—Mg—H-ZSM-5. A paste was prepared by adding 2.5% nitric acid (nitric acid solution/zeolite wt. ratio=1.2) to boehmite (boehmite/zeolite wt. ratio=1.5). To this paste, the above NaMgH type zeolite particles and water (water/zeolite wt. ratio=0.5) were added and extruded. It was dried at 120° C. for 12 hours and calcined at 550° C. for 12 hours to obtain a catalyst.

Then, a dehydration reaction of methanol was performed under the same reaction condition as in Example 1. The results are shown in Table 1.

EXAMPLE 6

A catalyst was prepared and a dehydration reaction of methanol was done using the same method as in Example 1, except for the reaction temperature which was changed to 250° C. The results are shown in Table 1.

EXAMPLE 7

A catalyst was prepared and a dehydration reaction of methanol was performed using the same method as in Example 1, except for the LHSV of the reaction which was maintained at 30 $h^{-1}$. The results are shown in Table 1.

EXAMPLE 8

A catalyst was prepared and a dehydration reaction of methanol was done using the same method as in Example 1, except for the LHSV for the reaction which was maintained at 30 $h^{-1}$ and the reaction temperature which was maintained at 250° C. The results are shown in Table 1.

EXAMPLE 9

To H-ZSM-5 ($SiO_2/Al_2O_3$=40) zeolite, boehmite (boehmite/zeolite wt. ratio=1) was added, followed by the addition of 2.5% aqueous nitric acid (nitric acid solution/zeolite wt. ratio=0.8) and water (water/zeolite wt. ratio=0.5) to obtain a paste which was then extruded, dried at 120° C. for 12 hours, and calcined at 550° C. for 12 hours. To the extrudates thus obtained, 6% aqueous ammonium hydroxide solution (ammonium hydroxide solution/extrudate wt. ratio=0.8) was added, dried at 120° C. for 12 hours and calcined at 350° C. for 2 hours to obtain finally a catalyst.

Then, a dehydration reaction of methanol was performed under the same reaction condition as in Example 1. The results are shown in Table 1.

EXAMPLE 10

H-ZSM-5 ($SiO_2/Al_2O_3$=40) zeolite was impregnated with aqueous sodium nitrate solution containing $Na^{3+}$ equivalent to 80 mole % of $H^+$ in the zeolite, dried at 120° C. for 12 hours, and calcined at 600° C. for 6 hours to obtain a Na—H-ZSM-5. Above NaH type zeolite was mixed with Ludox colloidal silica (silica/zeolite wt. ratio=0.25), and water (water/zeolite wt. ratio=0.7) was added to obtain a paste. The paste was extruded, dried at 120° C. for 12 hours, and calcined at 600° C. for 6 hours to obtain a catalyst.

A dehydration reaction of methanol was done using the same method as in Example 1, except for using methanol containing 20 mole % of water and the LHSV of the reaction which was maintained at 10 $h^{-1}$. The results are shown in Table 1.

EXAMPLE 11

H-ZSM-5 ($SiO_2/Al_2O_3$=90) zeolite was mixed with aqueous sodium nitrate solution containing $Na_+$ equivalent to 40 mole % of $H^+$ in the zeolite and silica-alumina (Kaolin Clay: $SiO_2$=45.42%, $Al_2O_3$=38.79%, CaO=0.35%, $Na_2O$=0.13%, $K_2O$=0.12%) (silica-alumina/zeolite wt. ratio=0.25). To this, water (water/zeolite wt. ratio=0.8) was added to obtain a paste. The paste was extruded, dried at 120° C. for 12 hours, and calcined at 600° C. for 6 hours to obtain a catalyst.

A dehydration reaction of methanol was done using the same method as in Example 1, except for using methanol containing 20 mole % of water and the LHSV of the reaction which was maintained at 10 $h^{-1}$. The results are shown in Table 1.

EXAMPLE 12

H-ZSM-5 ($SiO_2/Al_2O_3$=40) zeolite was mixed with aqueous sodium nitrate solution containing $Na^+$ equivalent to 20 mole % of $H^+$ in the zeolite and silica-alumina (Kaolin Clay: $SiO_2$=45.42%, $Al_2O_3$=38.79%, CaO=0.35%, $Na_2O$=0.13%, $K_2O$=0.12%) (silica-alumina/zeolite wt. ratio=1.5). To this, water (water/zeolite wt. ratio=1.6) was added to obtain a paste. The paste was extruded, dried at 120° C. for 12 hours, and calcined at 750° C. for 6 hours to obtain a catalyst.

A dehydration reaction of methanol was done using the same method as in Example 1, except for using methanol containing 20 mole % of water, the LHSV of the reaction which was maintained at 20 $h^{-1}$ and the reaction temperature which was maintained at 290° C. The results are shown in Table 1.

EXAMPLE 13

H-ZSM-5 ($SiO_2/Al_2O_3$=90) zeolite was mixed with aqueous sodium nitrate solution containing $Na^+$ equivalent to 40 mole % of $H^+$ in the zeolite and silica-alumina (Kaolin Clay: $SiO_2$=45.42%, $Al_2O_3$=38.79%, CaO=0.35%, $Na_2O$=0.13%, $K_2O$=0.12%) (silica-alumina/zeolite wt. ratio=1:0.25). To this, carboxymethyl cellulose (carboxymethyl cellulose/zeolite wt. ratio=0.02) and water (water/zeolite wt. ratio=1) was added to obtain a paste. The paste was extruded, dried at 120° C. for 12 hours, and calcined at 600° C. for 6 hours to obtain a catalyst.

A dehydration reaction of methanol was done using the same method as in Example 1, except for using methanol containing 20% water and the LHSV of the reaction which was maintained at 10 $h^{-1}$. The results are shown in Table 1.

COMPARATIVE EXAMPLE 1

H-ZSM-5 ($SiO_2/Al_2O_3$=40) zeolite was mixed with boehmite (boehmite/zeolite wt. ratio=1). To this, 2.5% aqueous nitric acid (nitric acid solution/zeolite wt. ratio=0.8) and water (water/zeolite wt. ratio=0.5) were added to obtain a paste. The paste was extruded, dried at 120° C. for 12 hours, and calcined at 600° C. for 6 hours to obtain a catalyst.

A dehydration reaction of methanol was done using the sane method as in Example 1. The results are shown in Table 1.

COMPARATIVE EXAMPLE 2

H-ZSM-5 ($SiO_2/Al_2O_3=40$) zeolite was impregnated with aqueous sodium nitrate solution containing $Na^+$ equivalent to 10 mole % of $H^+$, dried at 120° C. for 12 hours, and calcined at 600° C. for 6 hours to obtain a Na—H-ZSM-5. A paste was prepared by adding 2.5% nitric acid (nitric acid solution/zeolite wt. ratio=0.8) to boehmite (boehmite/zeolite wt. ratio=1). To this paste, the above NaH type zeolite particles and water (water/zeolite wt. ratio=0.5) were added and extruded. It was dried at 120° C. for 12 hours and calcined at 600° C. for 6 hours to obtain a catalyst.

A dehydration reaction of methanol was done using the same method as in Example 1. The results are shown in Table 1.

COMPARATIVE EXAMPLE 3

Na-ZSM-5 ($SiO_2/Al_2O_3=40$) zeolite was mixed with boehmite (boehmite/zeolite wt. ratio=1). To this, 2.5% aqueous nitric acid (nitric acid solution/zeolite wt. ratio=0.8) and water (water/zeolite wt. ratio=0.5) were added to obtain a paste. This paste was extruded, dried at 120° C. for 12 hours, and calcined at 600° C. for 6 hours to obtain a catalyst.

A dehydration reaction of methanol was done using the same method as in Example 1. The results are shown in Table 1.

COMPARATIVE EXAMPLE 4

H-ZSM-5 ($SiO_2/Al_2O_3=40$) zeolite was impregnated with aqueous sodium nitrate containing $Na^+$ equivalent to 40 mole % of $H^+$ in the zeolite, dried at 120° C. for 12 hours, and calcined at 600° C. for 6 hours to obtain a Na—H-ZSM-5. This NaH type zeolite was shaped into pellets using a pelletizer.

A dehydration reaction of methanol was done using the same method as in Example 1. The results are shown in Table 1.

The zeolites, binders and their weight ratios used in catalyst synthesis according to Examples 1-13 and Comparative Examples 1-4 as well as the results of the methanol dehydration reaction conducted using the catalysts manufactured thereof are shown in Table 1.

TABLE 1

| | Catalyst | | Yield (%) | |
|---|---|---|---|---|
| Classification | Zeolite | Binder (weight ratio*) | Dimethyl ether | Hydrocarbon |
| Example 1 | Na—H-ZSM-5 | Alumina (1) | 88.5 | 0.0 |
| Example 2 | Na—H-ZSM-5 | Alumina (1) | 87.9 | 0.0 |
| Example 3 | K—H-Beta | Alumina (1) | 75.3 | 0.0 |
| Example 4 | Ca—H-Mordenite | Alumina (1) | 78.1 | 0.0 |
| Example 5 | Na—Mg—H-ZSM-5 | Alumina (1.5) | 88.4 | 0.0 |
| Example 6 | Na—H-ZSM-5 | Alumina (1) | 89.2 | 0.0 |
| Example 7 | Na—H-ZSM-5 | Alumina (1) | 83.7 | 0.0 |
| Example 8 | Na—H-ZSM-5 | Alumina (1) | 81.7 | 0.0 |
| Example 9 | $NH_4$—H-ZSM-5 | Alumina (1) | 88.2 | 0.0 |
| Example 10 | Na—H-ZSM-5 | Silica (0.25) | 80.6 | 0.0 |
| Example 11 | Na—H-ZSM-5 | Silica-Alumina (0.25) | 82.1 | 0.0 |
| Example 12 | Na—H-ZSM-5 | Silica-Alumina (1.5) | 80.2 | 0.0 |
| Example 13 | Na—H-ZSM-5 | Silica-Alumina (0.25), CMC (0.02) | 82.5 | 0.0 |
| Comparative Example 1 | H-ZSM-5 | Alumina (1) | 22.0 | 78.0 |
| Comparative Example 2 | Na—H-ZSM-5 | Alumina (1) | 41.3 | 58.7 |
| Comparative Example 3 | Na-ZSM-5 | Alumina (1) | 27.0 | 0.0 |
| Comparative Example 4 | Na—H-ZSM-5 | — | 63.4 | 29.1 |

*weight ratio: the amount of a binder used per 1 weight part of zeolite

As shown in Table 1, the dehydration reactions of methanol using the catalysts manufactured in Examples 1 through 13 show very high yields of dimethyl ether and no hydrocarbon by-product is obtained.

On the other hand, the use of the catalyst obtained by mixing boehmite and H-ZSM-5 not impregnated with alkali metal, alkaline earth metal, or ammonium cations (Comparative Example 1), showed a poor selectivity with 22% yield of dimethyl ether along with a high yield of hydrocarbon (78%).

The catalyst with a small amount of sodium cation corresponding to 10 mole % with respect to the proton in zeolite (Comparative Example 2) also showed a low selectivity with a low yield of dimethyl ether (41.3%) with a significant production of hydrocarbon (58.7%).

The hydrocarbon side products of the Comparative Example 1 and 2 are of low molecular weights with low value and not desirable because they result in carbon deposition causing the deactivation of the catalyst.

For the catalyst obtained by mixing Na-ZSM-5 and boehmite (Comparative Example 3), the reaction yield of dimethyl ether was low at 27%. This results because zeolite itself does not show activity due to the very weak acidity of Na-ZSM-5, but the boehmite, which is mixed as a binder, is converted into gamma alumina, and this form is somewhat active.

An inorganic binder was not used in the Comparative Example 4 resulting in the formation of hot spots within the interior of the catalyst. This resulted in local temperature increases so that the reaction proceeded further resulting in the hydrocarbon formation. This resulted in a significantly lowered selectivity.

REFERENCE EXAMPLE 1

Mixtures of known catalysts for methanol synthesis $CuO/ZnO/Cr_2O_3/Al_2O_3$ (50/43/2/5 wt %) and the catalyst of Example 1 of this invention were used as a mixed catalyst for the synthesis of dimethyl ether from a mixture of hydrogen gas and carbon oxides.

The known catalyst for methanol synthesis and the catalyst of Example 1 were mixed in 1:1 wt. ratio, and a gas mixture of CO (4%), $CO_2$ (22.3%), and $H_2$ (73.7%) was used as a starting material. The dimethyl ether synthesis reaction was performed under the reaction temperature of 250° C., reaction pressure of 30 atm, and space velocity of 1500 ml/gh. The production of hydrocarbon was not observed, dimethyl ether was obtained in 24% yield, and the yield did not decrease for 150 hours.

REFERENCE EXAMPLE 2

A mixture of the known catalyst for methanol synthesis $CuO/ZnO/Cr_2O_3/Al_2O_3$ (50/43/2/5 wt %) and the catalyst of Comparative Example 1 of this invention were used as a mixed catalyst for the synthesis of dimethyl ether from a mixture of hydrogen gas and carbon oxides. And, dimethyl ether was synthesized using the same method as in above Reference Example 1. A mixture of 1% hydrocarbon and 23% dimethyl ether was obtained as the product. The production of dimethyl ether decreased with time resulting in 3% reduction of dimethyl ether yield after 150 hours because of the deactivation of the catalyst due to hydrocarbon production.

Therefore, the use of the catalyst of this invention along with the known catalysts for the methanol synthesis results in a relatively higher yield of dimethyl ether without any formation of hydrocarbon by-products.

INDUSTRIAL APPLICABILITY

As mentioned above, the acidity of zeolite is adjusted by incorporating cations selected from the group consisting of alkali metal, alkaline earth metal, and ammonium into hydrophobic zeolite. And, alumina, silica, and silica-alumina are used as binders as well as diluents to prevent local temperature increases due to hot spots during exothermic dehydration reaction in order to prevent the formation of hydrocarbon and carbon side products. Thus, an increased production yield of dimethyl ether is obtained due to the high catalytic activity without the hydrocarbon by-product formation when dimethyl ether is synthesized from methanol or gas mixtures.

What is claimed is:

1. A catalyst for dimethyl ether synthesis via dehydration reaction of methanol comprising: (a) hydrophobic zeolite with proton; (b) cations selected from the group consisting of alkali metal, alkaline earth metal, and ammonium; and (c) inorganic binders selected from the group consisting of alumina, silica, and silica-alumina.

2. The catalyst for dimethyl ether synthesis according to claim 1, wherein the $SiO_2/Al_2O_3$ ratio of said hydrophobic zeolite is between 20 and 200.

3. The catalyst for dimethyl ether synthesis according to claim 1, wherein said cations are impregnated in the range of from 20 to 90 mole % with respect to proton of the hydrophobic zeolite.

4. The catalyst for dimethyl ether synthesis according to claim 1, wherein said inorganic binders are contained in the range of from 0.5 to 50 wt. ratio with respect to the zeolite impregnated with cations selected from the group consisting of alkali metal, alkaline earth metal, and ammonium.

5. The catalyst for dimethyl ether synthesis according to claim 1, wherein said silica-alumina is clay.

6. The catalyst for dimethyl ether synthesis according to claim 1, wherein said catalyst is prepared in the form of granules, extrudates, tablets, balls, and pellets.

7. A method for manufacturing a catalyst for dimethyl ether synthesis comprising,
    (1-i) adding an aqueous acidic solution or water to at least one inorganic binder selected from the group consisting of boehmite, silica sol, and clay in order to convert the mixture into pastes;
    (1-ii) extrusion of said pastes to form a shape after mixing them with hydrophobic zeolite particles and salts or hydroxides of alkali metal or alkaline earth metal; and
    (1-iii) drying said formed product and calcining it at 500-800° C.

8. The method for manufacturing a catalyst according to claim 7, wherein said aqueous acidic solution is at least one aqueous acidic solution selected from the group consisting of nitric acid, acetic acid, and phosphoric acid.

9. The method for manufacturing a catalyst according to claim 7, wherein an organic binder selected from polyvinyl alcohol and carboxymethyl cellulose is further added during the step of said (1-i) or (1-ii).

10. The method for manufacturing a catalyst according to claim 7, wherein said salts of alkali metal or alkaline earth metal are nitrate or carbonate salts.

11. A method for manufacturing a catalyst for the synthesis of dimethyl ether comprising,
    (2-i) impregnating salts or hydroxides of alkali metal or alkaline earth metal into hydrophobic zeolite, drying the resultant and calcining it at 400-800° C. to obtain solid particles;
    (2-ii) adding an aqueous acidic solution or water to at least one inorganic binder selected from the group consisting of boehmite, silica sol, and clay in order to convert the mixture into pastes;
    (2-iii) extrusion of said solid particles and pastes to form a shape; and
    (2-iv) drying said formed product and calcining it at 500-800° C.

12. The method for manufacturing a catalyst according to claim 11, wherein said aqueous acidic solution is at least one aqueous acidic solution selected from the group consisting of nitric acid, acetic acid, and phosphoric acid.

13. The method for manufacturing a catalyst according to claim 11, wherein an organic binders selected from polyvinyl alcohol and carboxymethyl cellulose is further added in the step of said (2-i) or (2-iii).

14. The method for manufacturing a catalyst according to claim 11, wherein said alkali metal or alkaline earth metal salts are nitrate or carbonate salts.

15. A method for manufacturing a catalyst for the synthesis of dimethyl ether, wherein
    (3-i) adding an aqueous acid solution or water to at least one inorganic binder selected from the group consisting of boehmite, silica sol, and clay in order to convert the mixture into pastes;
    (3-ii) extrusion of the mixture of said pastes and hydrophobic zeolite particles to form a shape;
    (3-iii) drying said formed product and calcining it at 500-800° C.;

(3-iv) impregnating an aqueous solution of ammonium hydroxide or ammonium salts into said formed product;

(3-v) calcining said impregnated formed product at 300-400° C.

16. The method for manufacturing a catalyst according to claim 15, wherein said aqueous acid solution is at least one aqueous acid solution selected from the group consisting of nitric, acetic, and phosphoric acids.

17. The method for manufacturing a catalyst according to claim 15, wherein an organic binder selected from polyvinyl alcohol and carboxymethyl cellulose is further added in the step of said (3-i) and (3-ii).

* * * * *